United States Patent [19]

Puskas et al.

[11] 4,220,746

[45] Sep. 2, 1980

[54] 4-PEROXYESTER DERIVATIVES OF TRIMELLITIC ANHYDRIDE

[75] Inventors: Imre Puskas, Glen Ellyn; Ellis K. Fields, River Forest, both of Ill.

[73] Assignee: Standard Oil Company (Indiana), Chicago, Ill.

[21] Appl. No.: 908,111

[22] Filed: May 22, 1978

[51] Int. Cl.$^2$ .................. C07D 307/89; C07D 405/14
[52] U.S. Cl. ................................. 526/265; 260/346.3; 526/204; 526/328.5; 526/329.2; 526/329.7; 526/346; 526/347; 546/256
[58] Field of Search ...................... 260/346.3, 453 RZ; 546/256; 526/204, 265, 328.5, 329.2, 329.7, 346, 347

[56] References Cited

U.S. PATENT DOCUMENTS

| | | | |
|---|---|---|---|
| 2,567,615 | 9/1951 | Milas | 260/453 |
| 3,082,236 | 3/1963 | Mageli et al. | 260/453 RZ |
| 3,435,060 | 3/1969 | Johannes | 260/453 RZ |
| 4,029,685 | 6/1977 | Priddy | 260/453 RZ |

OTHER PUBLICATIONS

Tobolsky et al., Organic Peroxides, Their Chemistry, Decomposition and Role in Polymerization, Interscience Publishers, Inc., New York (1954) p. 37.

Hawkins, Organic Peroxides, Their Formation and Reactions, E. of F. F. Spon Ltd., London (1961) pp. 23 and 24.

Davies, Organic Peroxides, Butterworths, London (1961), pp. 58 and 59.

*Primary Examiner*—Richard Raymond
*Attorney, Agent, or Firm*—William C. Clarke; William T. McClain; William H. Magidson

[57] ABSTRACT

4-Peroxyester derivatives of trimellitic anhydride and polymers derived by use of these derivatives as dual function reagents for polymerization and introduction of the phthalic anhydride moiety.

13 Claims, No Drawings

4-PEROXYESTER DERIVATIVES OF TRIMELLITIC ANHYDRIDE

BACKGROUND OF THE INVENTION

This invention relates to a new composition of matter which is a peroxyester derivative of trimellitic anhydride and an alkyl hydroperoxide having the structural formula

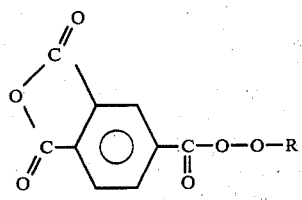

wherein R is a primary, secondary or tertiary alkyl group of 1 to 10 carbon atoms in the carbon chain.

Thermal decomposition of peresters has been shown to involve the rupture of the —O—O— bond, in some cases with simultaneous decarboxylation (P. D. Bartlett et al, *J.A.C.S.*, 80 1398)). Accordingly, the compounds of structural formula I of the perester decompose as shown by Equations 1 and 2.

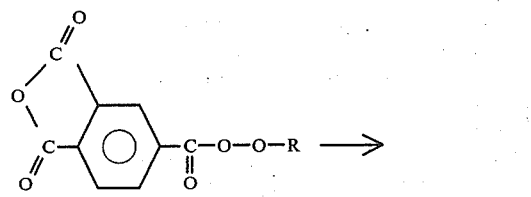
(1)

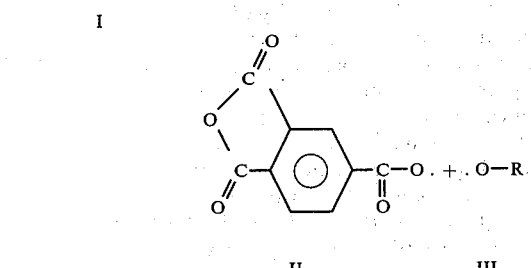

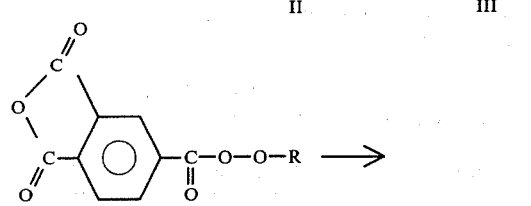
(2)

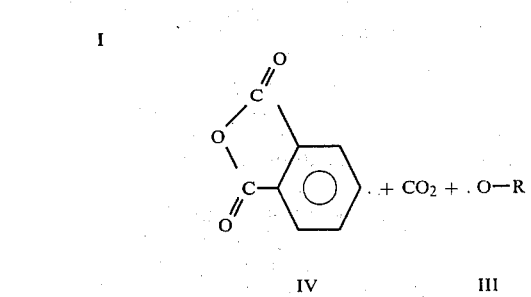

The radicals II, III and IV in the presence of monomers polymerizable by a radical mechanism can initate the terminate polymerization and thereby become attached to the ends of the polymer chain. This invention accordingly relates particularly to the attachment of the radicals II and IV to the ends of the polymer chain, thus introducing anhydride groups to the chain ends. By increasing the amount of the peroxide up to the level tolerated by the solubility in the particular monomer, polymers carrying various amounts of functional anhydride groups can be obtained. For example, an increase in the amount of the peroxide I will lower the molecular weight while increasing the anhydride content.

The general formula of the resulting polymers can be written as V or VI where M represents the divalent radical and repeating unit of the monomer (styrene, substituted styrene, acrylonitrile, acrylic esters, methacrylic esters, vinyl acetate, vinyl chloride, etc.), n is an integer between 2 and 10,000, and R is a primary, secondary or tertiary alkyl group.

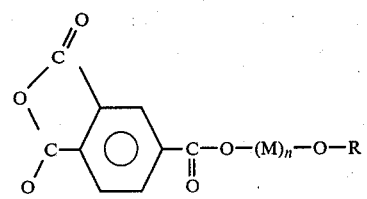

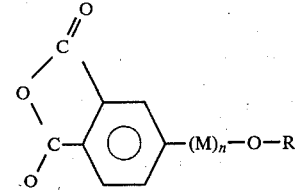

It is understood that, although the bulk of the polymer will be represented by formulae V and VI, molecules of different composition will also be present, i.e., both ends of the molecule can be terminated by the same radical, either II or III or IV. In addition II or III or IV can be missing from the chain ends due to competing initiation and termination reactions.

The polymers prepared by this invention find a wide range of application. The lower molecular weight polymers obtained by using larger quantities of the peroxide I can find application as detergents, rust inhibitors, oil additives (dispersants, rust inhibitors, V.I. improvers). For certain applications, it might be advantageous to hydrolyze the anhydride groups of V or VI by steam. If reacted with a diamine, condensation reaction takes place between the anhydride and amine groups. Application of this reaction can be in binding and gluing surfaces, and in modifying and grafting polymers.

In further detail, specific applications of the compounds of the instant invention lie in functional fluids such as hydraulic oils and in plasticizers.

Oils used as functional fluids must be extremely stable to temperature and pressure but their viscosity index must be low because the equipment must operate as a function of the viscosity index. A fully saturated ester of 500 to 50,000 molecular weight which is not subject to oxidation and does not contain either phosphorus or sulfur and accordingly is not corrosive is highly desirable. Additionally, an ester which is not a polychlorinated compound offers advantages of environmental protection if disposal is required.

Phthalic moiety-containing esters of suitable carbon chain length, i.e., from 500 to 50,000 molecular weight which have no volatility, such as the phthalate esters of this invention are very desirable as permanent plasticizers for polyvinyl chloride resins. Permanence is determined, among other characteristics, by low plasticizer volatility. The compounds of this invention as plasticizers have this property.

SUMMARY OF THE INVENTION

4-Perester derivatives of trimellitic anhydride and polymers derived by use of these derivatives as dual function reagents for polymerization and introduction of the phthalic anhydride moiety.

DETAILED DESCRIPTION OF THE INVENTION

The compositions of this invention are the 4-perester derivatives of trimellitic anhydride and alkyl hydroperoxides wherein the alkyl moiety is selected from primary, secondary and tertiary alkyl moieties of one to 10 carbon atoms in the carbon chain. Accordingly, the alkyl moiety can be methyl, ethyl, propyl, isopropyl, n-butyl, sec-butyl, tertiary butyl, amyl, tert-octyl, tert-nonyl, and n-decyl. The alkyl moieties can be substituted or unsubstituted. Since the reaction site between the trimellitic anhydride molecule and the alkyl hydroperoxide involves only the hydroperoxy moiety of the peroxide, the remainder of the peroxide molecule can be substituted with any substituents that do not interfere with the course of the reaction between the anhydride and with which the hydroperoxide moiety is not unstable or subject to rapid decomposition. Accordingly, other substituents which can be in the hydroperoxide reactant are fluorine, chlorine, and nitro moieties. Typical examples of these hydroperoxides and fluoro-tert-butyl hydroperoxide and 2-nitro-tert-amyl hydroperoxide.

Broadly speaking, the 4-peroxyester derivatives of trimellitic anhydride are prepared by reacting trimellitic anhydride and alkyl hydroperoxides. Alkyl hydroperoxides can be prepared by treating an olefin or an alcohol with hydrogen peroxide in the presence of an acid (usually sulfuric acid). t-Butyl hydroperoxide is prepared by reacting t-butyl alcohol with hydrogen peroxide in the presence of sulfuric acid.

The preparation of peroxyesters is well known as many peroxyester compounds have been prepared in the prior art. General approaches to peroxyesters can be by a Schotten-Baumen procedure at a temperature of 0° C. or lower which employs either aqueous alkali or pyridine as a base and utlizes either an acid anhydride or an acid chloride in the presence of the alkyl hydroperoxide. Another approach uses imidazolides as reactive intermediate. These are prepared from the carboxylic acid and either thionyl or N,N'-carbonyldiimidazole which are reacted with the alkyl hydroperoxide. Other methods of preparing peroxyesters are also well known but general application has been hampered by apparent thermal lability of the products.

In detail, the 4-alkyl trimellitic anhydrides are prepared by esterifying a trimellitic anhydride monoacid halide with an alkyl hydroperoxide, by maintaining the reactant mixture at a temperature low enough to prevent side reactions, in the presence of a tertiary amine and in the presence of a hydrocarbon solvent of sufficient solubility to solubilize the reactants and the tertiary amine wherein the said reactants consist essentially of the monoacid halide of trimellitic anhydride and 4-alkyl hydroperoxide where the alkyl moiety is selected from the group consisting of primary, secondary and tertiary alkyl moieties of one to 10 carbon atoms in the carbon chain. Preferably the alkyl moiety is selected from the group consisting of methyl, ethyl, propyl, isopropyl, n-butyl, sec-butyl, tert-butyl, amyl, tert-octyl, tert-nonyl and n-decyl moieties. Preferably the temperature is maintained below a temperature of about 15° C. although the temperature can be as high as 50° C. Preferred monoacid halide of trimellitic anhydride is the bromide or chloride. Preferred tertiary amine when the alkyl moiety is a tertiary butyl moiety is pyridine because of low solubility of the pyridine salt which results as a reaction product. Preferred solvent in the presence of pyridine, the monoacid chloride of trimellitic anhydride and 4-alkyl hydroperoxide wherein the alkyl moiety is tertiary butyl is benzene. Preferred ratio of tertiary amine to monoacid halide of trimellitic anhydride is mole for mole, 1:1, as the tertiary amine hydrohalide is formed as an end product. Preferably, the solvent is chosen so that the hydrohalide salt is insoluble in the solvent and precipitates.

Purification procedures of peroxyesters are limited by their thermal lability. Vacuum distillation can be used with low molecular weight liquids while the higher molecular weight oils are typically isolated by chromatographic procedures using a non-polar medium. Florisil, an absorbent containing a magnesia-silica gel catalyst, Floridin Company, Pittsburgh, Penna. is often used.

Evidence of the presence of peroxyesters is often by means of infrared spectroscopy. Peroxyesters display a characteristic band in the infrared region at about 1770 $cm^{-1}$. The approximate purity of a peroxyester can be indicated by infrared spectroscopy as the major contaminants usually contain carbonyl or hydroxyl groups. The peroxide number which is obtained by titrating liberated iodine of a potassium iodide solution with a standard thiosulfate solution also can indicate degree of purity. The calculated peroxide number of the pure peroxyester compared with peroxide number obtained by titrating the liberated iodine indicates relative purity in the presence of organic substances.

Peroxyesters are well-known as initiators in all major types of polymerization systems, such as bulk, solution, suspension or emulsion polymerizations in that peroxyesters are sources of free radicals. Temperature range in which the peroxyesters decompose largely determine the type of application. Thermal stability, compatibility with monomer systems, ease of activation, and efficiency and type of free radicals produced determine application and range of application. In addition, the peroxyesters of trimellitic anhydride introduce phthalic anhydride moieties into the polymer. Presence of an anhydride group at the end of the polymer chain permits cross-linking by the acyl groups. Lower molecular weight polymers with unreacted acyl groups are surface-active agents and dispersants. Higher molecular weight polymers are useful as oil additives.

Specifically, the 4-tert-butyl pertrimellitate anhydride, wherein R is tert-butyl, was prepared. This compound brought about the polymerization of styrene, methyl methacrylate, and 4-vinyl pyridine with simultaneous introduction of phthalic anhydride moieties.

Embodiments of the present invention can be found in the following examples. These embodiments and examples are presented for purposes of illustration only and are not intended to limit the scope of the invention.

EXAMPLE I

To a stirred, cooled solution of trimellitic anhydride acid chloride (10.6 g) in benzene (100 ml) was added dropwise a solution of anhydrous tert-butylhydroperoxide (4.5 g) in benzene (50 ml) and anhydrous pyridine (4.1 ml) at 6° C. After ¾ hour stirring the white precipitate was filtered off and washed with a little benzene. The combined filtrate and washings were passed through a small Florisil column and eluted with benzene. Removal of solvents in vacuo gave a glassy semi-solid product, 11.6 g. Its IR spectrum in the carbonyl region showed bands at 1867, 1810, 1783, and 1762 cm$^{-1}$ as a neat syrupy liquid. The NMR spectrum confirmed the presence of the tert-butyl group. Peroxide number, mls of normal sodium thiosulfate solution per one gram of sample was 6.0 milliequivalents per gram; this corresponds to 79% purity. This crude perester decomposed violently if placed into a 130° C. bath but decomposition was hardly observable if it was heated up slowly. For practical applications this perester is most conveniently handled in benzene solution.

In a thermal stability study, 3.0 g crude perester was refluxed in 20 ml benzene for 2½ hours. On standing at 6° C. for 16 hours the solution deposited slightly impure crystals of trimellitic anhydride (0.75 g; IR evidence). The starting perester was the major and only identifiable component of the benzene solution on the basis of IR spectrum.

EXAMPLE II

Styrene (10.0 g, stabilized with tert-butylcatechol) containing 1.0 g of 79% pure tert-butyl pertrimellitate anhydride (I, R=tert-butyl) was bulk-polymerized in a capped vial under nitrogen for 15½ hours at 65° C. followed by 106° for 16 hours. A brown, very tough solid resulted. (In a control experiment under identical conditions, but without the peroxide, styrene polymerized thermally to a viscous liquid only.) The peroxide-modified polystyrene did not loose any weight on vacuum drying (0.1 mm) overnight at room temperature. Infrared spectrum in carbon tetrachloride solution indicated the presence of anhydride and ester groups (1864, 1784 and 1738 cm$^{-1}$). The 1738 cm$^{-1}$ peak is theorized as due to an ester carbonyl as shown in V; it cannot be due to the starting perester I(R=tert. butyl), because under the conditions of the polymerization it must have decomposed (see thermal stability in Example I). A direct comparison of the IR spectra of the starting perester (I, R=tert. butyl) and of the polymer—although not available in the same solvent because of differing solubility—also suggested that the polymer contained the ester group. The modified polystyrene also showed carboxyl peak at 1705 cm$^{-1}$ that is theorized due to trimellitic anhydride, derived from radical II by hydrogen abstraction.

EXAMPLE III

Styrene (10.0 g) was bulk-polymerized in the presence of 0.35 g of the peroxide I (R=tert. butyl, 79% pure) under the conditions of Example II. A transparent solid polymer with a yellowish tint was obtained. Its IR spectrum in carbon tetrachloride solution showed peaks in the anhydride region at 1868, 1804 and 1785 cm$^{-1}$ whereas the product of Example II showed only a weak shoulder at 1804 cm$^{-1}$. This difference can be attributed to greater contribution of the structure VI to the polymer composition. Also, in the present example, the ester and the acid peaks at 1746 and 1705 cm$^{-1}$, respectively, were relatively weak.

EXAMPLE IV

Styrene was bulk-polymerized in nitrogen-purged, capped vials at 80° for 16 hours followed at 105° for 5 hours in the presence of different quantities of 76% pure tert-butyl pertrimellitate anhydride (I, R=tert-butyl). The products were analyzed by vacuum thermogravimetry (at 120 mm). The table shows the weight losses at 200° at 5°/min. heating rates.

| Wt. of 76% pure initiator per 10 g Monomer | Wt. loss of Polymer at 200° C. |
|---|---|
| (g) | (%) |
| 1.51 | 9.2 |
| 0.71 | 5.4 |
| 0.35 | 3.0 |

These data indicate that with increasing quantity to peroxide increasing quantities of lower molecular weight products were produced in agreement with the expectations.

EXAMPLE V

Methyl methacrylate (10.0 g) containing 1.517 g of 76% pure 4-tert. butyl pertrimellitate anhydride (I, R=tert. butyl) was bulk polymerized in a vial under nitrogen for 15½ hours at 73°, 5 hrs. at 93°, and slowly heated to 120° C. A transparent, slightly yellowish tough solid polymer was obtained. In a control experiment, methyl methacrylate without the peroxide remained a liquid. Vacuum thermogravimetry on the product showed 7.0% weight loss at 190° C. at 5° C./min. heating rate.

EXAMPLE VI

Methyl methacrylate (10.0 g) was bulk-polymerized in the presence of 0.70 g of the peroxide I (R=tert-butyl, 76% pure) under the conditions of Example V. A transparent, almost colorless, tough glassy solid was obtained. Vacuum thermogravimetry (120 mm) gave 3.6% weight loss at 190° (5°/min. heating rate).

EXAMPLE VII

Stabilized 4-vinylpyridine (10.0 g) was bulk-polymerized in the presence of 1.0 g of 79% pure I (R=tert. butyl) under nitrogen in a capped vial at room temperature for 16 hours, followed at 70° C. for one hour. A brown, brittle, fragile solid was obtained, soluble in pyridine. In a control experiment without the peroxide no observable change occurred with 4-vinyl pyridine. Infrared spectrum in pyridine solution showed only anhydride and acid carbonyl bands and only a shoulder at 1720 cm$^{-1}$ attributable to ester carbonyl.

What is claimed:

1. 4-Alkyl pertrimellitate anhydrides.
2. The compound of claim 1 wherein the alkyl group of the said compound contains up to 10 carbon atoms in the carbon chain.
3. The compound of claim 2 wherein the said alkyl group is a tert-butyl group.
4. A polymer of the structural formula

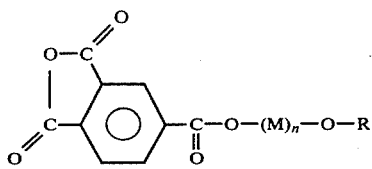

wherein M is a divalent monomer radical of a monomer compound selected from the group consisting of styrene, methyl methacrylate and 4-vinylpyridine, n is an integer from 2 to 10,000, and R is selected from the group consisting of a hydrogen moiety, an alkyl moiety of from one to ten carbon atoms and the moiety

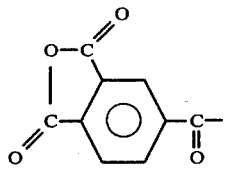

5. A polymer of the structural formula

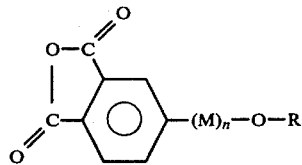

wherein M is a divalent monomer radical of a monomer compound selected from the group consisting of styrene, methyl methacrylate and 4-vinyl pyridine, n is an integer from 2 to 10,000 and R is selected from the group consisting of a hydrogen moiety, an alkyl moiety of from one to ten carbon atoms and the moiety

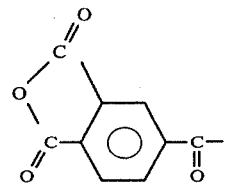

6. A process for preparing 4-alkyl pertrimellitate anhydrides which consists essentially of esterifying a trimellitic anhydride monoacid halide with an alkyl hydroperoxide which comprises maintaining the reactant mixture at a temperature sufficiently low to prevent side reactions, in the presence of a tertiary amine and in the presence of a hydrocarbon solvent wherein the alkyl moiety of said alkyl hydroperoxide is selected from the group consisting of primary, secondary and tertiary alkyl moieties of one to 10 carbon atoms in the carbon chain.

7. The process of claim 6 wherein the said trimellitic anhydride monoacid halide is selected from the group consisting of trimellitic anhydride monoacid chloride and trimellitic anhydride monoacid bromide.

8. The process of claim 6 wherein the said alkyl moiety is selected from the group consisting of methyl, ethyl, propyl, isopropyl, n-butyl, sec-butyl, tert-butyl, amyl, tert-octyl, tert-nonyl and n-decyl moieties.

9. The process of claim 6 wherein the said temperature is below about 50° C.

10. The process of claim 9 wherein the said temperature is below 15° C.

11. The process of claim 6 wherein the said tertiary amine is pyridine.

12. The process of claim 6 wherein the said alkyl hydroperoxide is tert-butyl hydroperoxide.

13. The process of claim 6 wherein the said solvent is benzene.

* * * * *

UNITED STATES PATENT OFFICE
CERTIFICATE OF CORRECTION

Patent No. 4,220,746  Dated September 2, 1980

Inventor(s) Imre Puskas and Ellis K. Fields

It is certified that error appears in the above-identified patent and that said Letters Patent are hereby corrected as shown below:

| Patent Column | Line | |
|---|---|---|
| 1 | 25 | "et al, J.A.C.S., 80 1398))." should be --et al, $\underline{\text{J.A.C.S.}}$, $\underline{80}$ 1398)).-- |
| 3 | 12 | "4-Perester" should be --4-Peroxyester-- |
| 3 | 38 | "and fluoro-tert" should be --are fluoro-tert-- |
| 3 | 20 | "4-perester" should be --4-peroxyester-- |
| 3 | 57 | "intermediate" should be --intermediates-- |
| 6 | 12 | "pertimellitate" should be --pertrimellitate-- |

UNITED STATES PATENT OFFICE
CERTIFICATE OF CORRECTION

Patent No. 4,220,746    Dated September 2, 1980

Inventor(s) Imre Puskas and Ellis K. Fields

It is certified that error appears in the above-identified patent and that said Letters Patent are hereby corrected as shown below:

| Patent Column | Line | |
|---|---|---|
| 6 | 24 | "quantity to" should be --quantity of-- |

Signed and Sealed this

Tenth Day of February 1981

[SEAL]

Attest:

RENE D. TEGTMEYER

Attesting Officer    Acting Commissioner of Patents and Trademarks